US009357768B2

(12) United States Patent
Fefer et al.

(10) Patent No.: US 9,357,768 B2
(45) Date of Patent: Jun. 7, 2016

(54) HERBICIDAL COMPOSITION WITH INCREASED HERBICIDAL EFFICACY

(75) Inventors: Michael Fefer, Whitby (CA); Jun Liu, Oakville (CA)

(73) Assignee: Suncor Energy Inc., Calgary, Alberta (CA)

( * ) Notice: Subject to any disclaimer, the term of this patent is extended or adjusted under 35 U.S.C. 154(b) by 1526 days.

(21) Appl. No.: 11/866,157

(22) Filed: Oct. 2, 2007

(65) Prior Publication Data

US 2008/0085832 A1   Apr. 10, 2008

Related U.S. Application Data

(60) Provisional application No. 60/828,352, filed on Oct. 5, 2006.

(51) Int. Cl.
*A01N 25/04* (2006.01)
*A01N 39/02* (2006.01)
*A01N 39/04* (2006.01)

(52) U.S. Cl.
CPC .............. *A01N 25/04* (2013.01); *A01N 39/02* (2013.01); *A01N 39/04* (2013.01)

(58) Field of Classification Search
None
See application file for complete search history.

(56) References Cited

U.S. PATENT DOCUMENTS

| | | |
|---|---|---|
| 2,714,062 A | 7/1955 | Lockrey |
| 2,786,821 A | 3/1957 | Gardner |
| 2,870,037 A | 1/1959 | Converse |
| 3,131,119 A | 4/1964 | Fordyce |
| 3,426,126 A | 2/1969 | Thorne et al. |
| 3,615,799 A | 10/1971 | Gannon |
| 3,689,574 A | 9/1972 | Engelhart |
| 3,799,758 A | 3/1974 | Franz |
| 3,948,635 A | 4/1976 | Vachette et al. |
| 3,950,265 A | 4/1976 | Albrecht |
| 3,997,322 A | 12/1976 | Ratledge |
| 4,002,628 A | 1/1977 | Benefiel |
| 4,015,970 A | 4/1977 | Hennart |
| 4,041,164 A | 8/1977 | Albrecht et al. |
| 4,094,845 A | 6/1978 | De Long |
| 4,124,720 A | 11/1978 | Wenmaekers |
| 4,243,405 A | 1/1981 | Balasubramanyan |
| 4,431,554 A | 2/1984 | Baur |
| 4,584,013 A | 4/1986 | Brunner |
| 4,618,360 A | 10/1986 | Brunner |
| 4,693,745 A | 9/1987 | Brunner |
| 4,698,334 A | 10/1987 | Horriere |
| 4,734,432 A | 3/1988 | Szego |
| 4,737,515 A | 4/1988 | Hallenbach et al. |
| 4,761,423 A | 8/1988 | Szego |
| 4,826,863 A | 5/1989 | Szego |
| 4,834,908 A | 5/1989 | Hazen |
| 4,853,026 A | 8/1989 | Frisch |
| 4,902,333 A | 2/1990 | Quimby |
| 4,971,840 A | 11/1990 | Boho |
| 5,084,087 A | 1/1992 | Hazen |
| 5,102,442 A * | 4/1992 | Hazen ................... A01N 25/02 504/110 |
| 5,137,726 A | 8/1992 | Ogawa |
| 5,178,795 A | 1/1993 | Roberts |
| 5,229,356 A | 7/1993 | Tocker |
| 5,238,604 A | 8/1993 | Hazen |
| 5,308,827 A | 5/1994 | Sakamoto |
| 5,330,995 A | 7/1994 | Eicken et al. |
| 5,336,661 A | 8/1994 | Lucas |
| 5,352,729 A | 10/1994 | Birkhofer |
| 5,362,167 A | 11/1994 | Loftin |
| 5,393,770 A | 2/1995 | Grayson |
| 5,393,791 A | 2/1995 | Roberts |
| 5,409,885 A | 4/1995 | Derian |
| 5,504,054 A | 4/1996 | Murphy |
| 5,547,918 A | 8/1996 | Newton |
| 5,558,806 A | 9/1996 | Policello et al. |
| 5,580,567 A | 12/1996 | Roberts |
| 5,599,768 A | 2/1997 | Hermansky |
| 5,599,804 A | 2/1997 | Mudge |
| 5,643,852 A | 7/1997 | Lucas |
| 5,658,851 A | 8/1997 | Murphy |
| 5,665,672 A | 9/1997 | Lucas |
| 5,668,086 A | 9/1997 | Tadayuki et al. |
| 5,703,016 A | 12/1997 | Magin |
| 5,739,371 A | 4/1998 | O'Lenick |
| 5,741,502 A | 4/1998 | Roberts |
| 5,919,858 A | 7/1999 | Loftin |
| 5,958,104 A | 9/1999 | Nonomura et al. |
| 6,033,647 A | 3/2000 | Touzan |

(Continued)

FOREIGN PATENT DOCUMENTS

| | | | |
|---|---|---|---|
| CA | 964482 | * | 3/1975 |
| CA | 2069311 | | 4/1991 |

(Continued)

OTHER PUBLICATIONS

McCowan, Turf Herbicide Rx: Add Oil, Ag Chem, Apr. 1968, pp. 18-21.*
Burr RJ and Warren GF, Weed Science 19(6): 701-705 (1971).*
Grover et al., Weed Science 20(4): 320-324 (1972).*
Burt, "Tolerance of Warmseason Turf Grasses to Herbicides," *Plantation Field Laboratory Mimeo Report PFL66-1*, 10 pages (Aug. 1966).
Horn, "Tolerance of Several Southern Turfgrasses to Various Spray Oils," *Florida State Horticultural Society*, pp. 494-499 (1966).

(Continued)

*Primary Examiner* — Robert A Wax
*Assistant Examiner* — Thor Nielsen
(74) *Attorney, Agent, or Firm* — Fish & Richardson P.C.

(57) ABSTRACT

An herbicide composition available as a concentrate for dilution with water or a ready-to-use oil-in-water emulsion which has a significantly reduced amount of active ingredient of a broadleaf herbicide. The composition combines the reduced amount of herbicide in a mixture of oil and emulsifier.

37 Claims, 1 Drawing Sheet

(56) References Cited

U.S. PATENT DOCUMENTS

| | | |
|---|---|---|
| 6,117,820 A | 9/2000 | Cutler |
| 6,146,652 A | 11/2000 | Gore |
| 6,159,900 A | 12/2000 | Bieringer |
| 6,162,763 A | 12/2000 | Tateno |
| 6,210,656 B1 | 4/2001 | Touzan |
| 6,221,811 B1 | 4/2001 | Policello |
| 6,329,321 B2 | 12/2001 | Okura |
| 6,403,061 B1 | 6/2002 | Candau |
| 6,416,748 B1 | 7/2002 | Candau |
| 6,432,877 B2 | 8/2002 | Okura |
| 6,515,031 B2 * | 2/2003 | Fefer ........................ 516/73 |
| 6,673,360 B2 | 1/2004 | Fefer |
| 6,683,030 B2 | 1/2004 | Kober |
| 6,713,518 B1 | 3/2004 | Bessette |
| 6,727,205 B2 | 4/2004 | Brinkman |
| 6,734,202 B2 | 5/2004 | Cotter |
| 6,803,345 B2 | 10/2004 | Herold |
| 6,878,674 B2 | 4/2005 | Kobayashi |
| 6,972,273 B2 | 12/2005 | Sedun et al. |
| 7,135,435 B2 | 11/2006 | Cooper |
| 7,799,343 B2 * | 9/2010 | Loughner ................ 424/489 |
| 7,923,452 B2 | 4/2011 | Birner et al. |
| RE42,394 E | 5/2011 | Mudge |
| 8,076,267 B2 | 12/2011 | Diebold et al. |
| 8,298,990 B2 | 10/2012 | Wu et al. |
| 8,426,343 B2 | 4/2013 | Norton et al. |
| 8,569,210 B2 | 10/2013 | Fefer et al. |
| 8,747,874 B2 | 6/2014 | Fefer |
| 8,748,342 B2 | 6/2014 | Gewehr et al. |
| 8,853,128 B2 | 10/2014 | Fefer et al. |
| 9,044,008 B2 | 6/2015 | Fefer |
| 2001/0019728 A1 | 9/2001 | Basinger |
| 2002/0161057 A1 | 10/2002 | Fefer |
| 2003/0087764 A1 | 5/2003 | Pallas |
| 2003/0187079 A1 | 10/2003 | Fefer |
| 2003/0194454 A1 | 10/2003 | Bessette |
| 2003/0198659 A1 | 10/2003 | Hoffmann |
| 2003/0198696 A1 | 10/2003 | Keen |
| 2004/0132621 A1 | 7/2004 | Frisch |
| 2004/0151749 A1 | 8/2004 | Hasebe et al. |
| 2004/0167034 A1 | 8/2004 | Coote |
| 2004/0192556 A1 * | 9/2004 | Schregenberger et al. ... 504/361 |
| 2005/0026786 A1 | 2/2005 | Deckwer |
| 2005/0181949 A1 | 8/2005 | Norton |
| 2005/0202102 A1 | 9/2005 | Miller |
| 2005/0233907 A1 | 10/2005 | Nabors |
| 2005/0261379 A1 | 11/2005 | Fefer |
| 2005/0274164 A1 | 12/2005 | Coates |
| 2006/0063676 A1 | 3/2006 | Brigance |
| 2006/0068991 A1 | 3/2006 | Norton |
| 2006/0194699 A1 | 8/2006 | Moucharafieh et al. |
| 2006/0276339 A1 | 12/2006 | Windsor |
| 2006/0282961 A1 | 12/2006 | Hughes |
| 2006/0293188 A1 | 12/2006 | Norton |
| 2007/0184005 A1 | 8/2007 | Policello |
| 2007/0197387 A1 | 8/2007 | Polge |
| 2007/0287720 A1 | 12/2007 | Royalty et al. |
| 2008/0064601 A1 | 3/2008 | Casanello et al. |
| 2008/0085832 A1 | 4/2008 | Fefer |
| 2008/0112909 A1 | 5/2008 | Faler |
| 2008/0153702 A1 | 6/2008 | Voeste |
| 2008/0161367 A1 | 7/2008 | Voeste |
| 2008/0280763 A1 | 11/2008 | Hodge |
| 2008/0293567 A1 | 11/2008 | Birner et al. |
| 2009/0325922 A1 | 12/2009 | Fefer |
| 2010/0016447 A1 | 1/2010 | Fefer |
| 2010/0317527 A1 | 12/2010 | Takeuchi et al. |
| 2011/0306495 A1 | 12/2011 | Sanaraheewa et al. |
| 2012/0245232 A1 | 9/2012 | Bousque et al. |
| 2013/0253016 A1 | 9/2013 | Fefer et al. |
| 2013/0303374 A1 | 11/2013 | Fefer et al. |
| 2013/0324620 A1 | 12/2013 | Fefer |
| 2014/0107070 A1 | 4/2014 | Fefer et al. |
| 2014/0228218 A1 | 8/2014 | Fefer et al. |
| 2014/0256556 A1 | 9/2014 | Fefer et al. |
| 2015/0065475 A1 | 3/2015 | Fefer et al. |
| 2015/0237869 A1 | 8/2015 | Fefer |

FOREIGN PATENT DOCUMENTS

| | | |
|---|---|---|
| CA | 2434848 A1 | 8/2002 |
| CA | 2496142 A1 | 8/2005 |
| CA | 2472806 A1 | 11/2005 |
| CA | 2507482 A1 | 11/2005 |
| CA | 2568817 | 12/2005 |
| CA | 2209920 | 1/2007 |
| CA | 2562718 A1 | 4/2008 |
| CA | 2605092 A1 | 4/2008 |
| CA | 2625415 | 9/2008 |
| CA | 2748084 | 7/2010 |
| CA | 2839775 | 6/2013 |
| CN | 101238820 | 8/2008 |
| CN | 101304658 | 11/2008 |
| CN | 101390517 | 3/2009 |
| CN | 101415327 A | 4/2009 |
| CN | 101473849 | 7/2009 |
| CN | 101998827 | 3/2011 |
| CN | 101773113 | 2/2013 |
| DE | 2511077 | 9/1976 |
| EP | 0267778 | 5/1988 |
| EP | 0498231 B2 | 8/1992 |
| EP | 0526206 | 2/1993 |
| EP | 0598515 B1 | 5/1994 |
| EP | 0862857 A1 | 9/1998 |
| EP | 1173059 B1 | 11/2000 |
| EP | 1563734 | 8/2005 |
| GB | 745360 A | 2/1956 |
| GB | 747909 A | 4/1956 |
| GB | 748422 A | 5/1956 |
| GB | 753976 A | 8/1956 |
| GB | 758926 A | 10/1956 |
| GB | 762866 A | 12/1956 |
| GB | 763246 A | 12/1956 |
| GB | 765459 A | 1/1957 |
| GB | 792045 A | 3/1958 |
| GB | 1044895 A | 10/1966 |
| GB | 1168913 | 10/1969 |
| GB | 1249674 A | 10/1971 |
| GB | 1417364 A | 12/1975 |
| GB | 1499397 | 2/1978 |
| GB | 2123819 A | 2/1984 |
| GB | 2176493 A | 12/1986 |
| JP | 50-063141 | 5/1975 |
| JP | 54-036205 | 11/1979 |
| JP | 55-129213 | 10/1980 |
| JP | 57028184 A | 2/1982 |
| JP | 59-067205 | 4/1984 |
| JP | 59-210007 | 11/1984 |
| JP | 2138376 A | 5/1990 |
| JP | 3183505 A | 8/1991 |
| JP | 3221576 A | 9/1991 |
| JP | 4128003 A | 4/1992 |
| JP | 7-179306 | 7/1995 |
| JP | 8218225 A | 8/1996 |
| JP | 10-29901 | 2/1998 |
| JP | 11137084 A | 5/1999 |
| JP | 11349588 | 12/1999 |
| JP | 2006-124337 | 5/2006 |
| JP | 2008-502640 | 1/2008 |
| NL | 8900381 | 9/1990 |
| SU | 1021415 | 6/1983 |
| WO | 9007272 A1 | 7/1990 |
| WO | 9312175 | 6/1993 |
| WO | WO 9621353 | 7/1996 |
| WO | 9632010 A2 | 10/1996 |
| WO | 9632011 A2 | 10/1996 |
| WO | 9835561 A1 | 8/1998 |
| WO | WO 0064257 | 11/2000 |
| WO | 0221913 A2 | 3/2002 |
| WO | WO 0234047 | 5/2002 |
| WO | 02089573 A1 | 11/2002 |
| WO | 02096199 A2 | 12/2002 |
| WO | 03101195 A1 | 12/2003 |

(56) References Cited

FOREIGN PATENT DOCUMENTS

| | | |
|---|---|---|
| WO | 03105587 A1 | 12/2003 |
| WO | 2004030641 A1 | 4/2004 |
| WO | 2004080177 A2 | 9/2004 |
| WO | 2005009132 A1 | 2/2005 |
| WO | WO 2005018324 | 3/2005 |
| WO | 2005055716 A2 | 6/2005 |
| WO | 2005082137 | 9/2005 |
| WO | WO 2006126211 | 11/2006 |
| WO | WO 2007054473 | 3/2007 |
| WO | 2007117720 A2 | 10/2007 |
| WO | 2007136597 A2 | 11/2007 |
| WO | 2008049192 A1 | 5/2008 |
| WO | 2008073397 A1 | 6/2008 |
| WO | WO 2009090181 | 7/2009 |
| WO | WO 2009126370 | 10/2009 |
| WO | WO 2009139106 | 11/2009 |
| WO | 2009155693 A1 | 12/2009 |
| WO | WO 2010043447 | 4/2010 |
| WO | WO 2010132169 | 11/2010 |
| WO | WO 2011028987 | 3/2011 |
| WO | WO 2011070503 | 6/2011 |
| WO | WO 2012031355 | 3/2012 |
| WO | WO 2012040804 | 4/2012 |
| WO | WO 2012055991 | 5/2012 |
| WO | WO 2012126094 | 9/2012 |
| WO | WO 2012162844 | 12/2012 |
| WO | WO 2012162846 | 12/2012 |
| WO | WO 2012171126 | 12/2012 |
| WO | WO 2013078546 | 6/2013 |
| WO | WO 2014139012 | 9/2014 |

OTHER PUBLICATIONS

Horn, "Increasing the Effectiveness of Turf Herbicides by Use of Oil," *Florida State Horticultural Society*, pp. 499-509 (1966).
Office Action dated Nov. 9, 2011 from Canadian Patent Application No. 2,507,482, 4 pages.
Office Action dated Nov. 10, 2011 from U.S. Appl. No. 12/563,929, 35 pages.
PureSpray Spray Oil 10E, Delaware Department of Agriculture Pesticide Database Searches (downloaded from DDA website Apr. 7, 2005).
Pesticide Product Label System (PPLS)—Search Results for PureSpray Oil 10E—Approval dates Apr. 21, 2000, Jul. 23, 2002, Sep. 24, 2003, Mar. 5, 2004 (downloaded from EPA Office of Pesticide Programs website Apr. 27, 2005).
Material Safety Data Sheet for Agri-Dex, Helena Chemical Company, Apr. 29, 2005.
Material Safety Data Sheet for Blendex VHC, Helena Chemical Company, Jul. 27, 2000.
Material Safety Data Sheet for Civitas, Petro-Canada Lubricants, Inc., Mar. 21, 2011.
Material Safety Data Sheet for Harmonizer, Petro-Canada Lubricants Inc., May 6, 2011.
Material Safety Data Sheet for JMS Stylet-Oil (Mar. 1, 1994).
Material Safety Data Sheet for Peptoil, Drexel Chemical Company, Jan. 7, 2005.
Material Safety Data Sheet for Surf Ac 820, Drexel Chemical Company, Jul. 22, 2005.
Specimen Label for Agri-Dex, Helena Chemical Company, 2005.
Specimen Label for Blendex VHC, Helena Chemical Company, 2006.
Specimen Label for Civitas, Petro-Canada Lubricants, Inc., (2007).
Specimen Label for Harmonizer, Petro-Canada Lubricants, Inc. (2007).
Specimen Label for Peptoil, Drexel Chemical Company, (2007).
Specimen Label for Sil-Fact, Drexel Chemical Company, (2007).
Specimen Label for Sil-MES 100, Drexel Chemical Company, (2007).
Specimen Label for Surf-Ac 820, Drexel Chemical Company, (2007).
2006 Pest Control Recommendations for Lawn and Turf Areas, Rutgers Cook College, http://njaes.rutgers.edu/pubs/publication.asp?pid=e037 (downloaded Aug. 25, 2011).
Leaflet for Volpo, Croda Chemicals Europe Ltd, http://www.chservice.ru/download/DC%20Volpo.pdf, (2007).
Brochure for Civitas, Petro-Canada, http://www.civitasturf.com/pdf/CIVITAS-technical-brochure.pdf (downloaded Aug. 22, 2011).
Technical Bulletin for Civitas, Petro-Canada, http://www.civitasturf.com/pdf/techBulletin.pdf (downloaded Aug. 22, 2011).
A Guide to Major Turfgrass Pests & Turfgrasses, NC State University, http://www.turffiles.ncsu.edu/PDFFiles/004041/ag348.pdf (downloaded Aug. 25, 2011).
Application of Fungicides for Suppression of *Fusarium* Head Blight (Scab), North Dakota State University, http://www.ag.ndsu.edu/pubs/ageng/machine/ae1148w.htm (downloaded Aug. 22, 2011).
An Integrated Approach to Insect Management in Turfgrass: Black Cutworm, Richard J. Buckley et al., Rutgers, The State University of New Jersey, http://snyderfarm.rutgers.edu/pdfs/BlackCutworms.pdf (downloaded Aug. 26, 2011).
An Integrated Approach to Insect Management in Turfgrass: Sod Webworms, Albrecht M. Koppenhofer et al., Rutgers, The State University of New Jersey, http://snyderfarm.rutgers.edu/pdfs/SodWebworms.pdf (downloaded Aug. 26, 2011).
An Integrated Approach to Insect Management in Turfgrass: White Grubs, Albrecht M. Koppenhofer et al., Rutgers, The State University of New Jersey, http://www.co.somerset.nj.us/_pdffiles/JapBeetleFS.pdf (downloaded Aug. 26, 2011).
Armyworms and cutworms in turfgrass, Erin W. Hodgson, Utah State University, http://extension.usu.edu/files/publications/factsheet/armyw-cutw-turf07.pdf (downloaded Aug. 26, 2011).
Bentgrass dead spot, University of Connecticut, http://www.turf.uconn.edu/pdf/research/factsheets/Disease_Bentgrass_Dead_Spot.pdf (downloaded Aug. 22, 2011).
Bentgrass Deadspot, Cornell University, http://plantclinic.cornell.edu/factsheets/bentgrassdeadspot.pdf (downloaded Aug. 22, 2011).
Biological/Biorational Products for Disease Management, University of Connecticut Integrated Pest Management, http://www.ipm.uconn.edu/ipm/greenhs/htms/biofung.htm (downloaded Aug. 22, 2011).
Biology and Control of Dollar Spot Disease, Ontario Ministry of Agriculture Food & Rural Affairs, http://www.omafra.gov.on.ca/english/crops/facts/info_turfdollarspot.htm (downloaded Aug. 22, 2011).
Black Cutworms, D.R. Smitley et al., Michigan State University Turfgrass Science, http://www.turf.msu.edu/black-cutworms (downloaded Aug. 26, 2011).
Chemical Control of Turfgrass Diseases 2011, University of Kentucky College of Agriculture, http://pest.ca.uky.edu/PSEP/Manuals/ppa1.pdf (downloaded Aug. 25, 2011).
Chemical Structures, The Bugwood Network, http://www.bugwood.org/PAT/22chemicalstructures.html (downloaded May 25, 2006).
Christians, Creative Uses for Plant Growth Regulators, USGA Green Section Record, 2001, Sep. 11-13/Oct. 2001.
Danneberger et al., Turfgrass Growth Substances, Golf Course Management, 1990, 80, 82, 86, 88, 58(4).
Grey et al., Timed Release of Flurprimidol from a Granular Formulation in Mulches and Sand, HortScience, 2009, 512-515, 44(2).
Huang, Plant growth regulators: What and why, GCM golf course management, 2007, 157-160, Jan. 2007.
Lickfeldt et al., Implications of Repeated Trinexapac-Ethyl Applications on Kentucky Bluegrass, Agronomy Journal, 2001, 1164-1168, 93(5).
Mercier, Use of the growth regulator paclobutrazol in the management of dollar spot of creeping bentgrass in Minnesota, Phytoprotection, 1999, 65-70, 80(2).
Chemical Trials for Dollar Spot Disease Control Summer 2006, Guelph Turfgrass Institute 2006 Annual Research Report, http://131.104.104.3/06anrep/40-42.pdf (downloaded Aug. 22, 2011).
Clover and Other Mites of Turfgrass, W.S. Cranshaw, Colorado State University, http://www.ext.colostate.edu/pubs/insect/05505.html (downloaded Aug. 26, 2011).
Cultural practices and their effects upon turf grass growth and stress tolerance, Greenkeeper International, http://www.bigga.org.uk/

(56) References Cited

OTHER PUBLICATIONS about-us/magazine/back-issues/07-2006/cultural-pray-tim-butler/00919.html (downloaded Aug. 24, 2011).
Dead Spot Disease of Creeping Bentgrass, University of Maryland, http://www.hgic.umd.edu/content/documents/TT-14DeadSpot.pdf (downloaded Aug. 22, 2011).
Dead Spot of Creeping Bentgrass and Hybrid Bermudagrass, Plant Management Network, http://www.plantmanagementnetwork.org/pub/ats/diagnostic/2005/deadspot/ (downloaded Aug. 22, 2011).
Dollar Spot on Turfgrass, Cornell University, http://counties.cce.cornell.edu/wyoming/agriculture/resources/ipd/dollar_spot_turfgrass.htm (downloaded Aug. 22, 2011).
EPA: Pesticides—Inert (other) Pesticide Ingredients in Pesticide Products, U.S. Environment Protection Agency, http://www.epa.gov/opprd001/inerts/lists.html (downloaded Sep. 11, 2007).
Fungicide Resistance Action Committee Code List: Fungicides sorted by mode of Action, Fungicide Resistance Action Committee, http://www.frac.info/frac/publication/anhang/FRAC%20Code%20List%202011-final.pdf (downloaded Aug. 22, 2011).
Fungicide Synergy, Kansas State University, http://www.ksuturf.com/LISTServArchive/2009_02_26_Fungicide_Synergy.pdf (downloaded Aug. 22, 2011).
Gray leaf spot of perennial ryegrass, Kansas State University Turfgrass Research, (downloaded Aug. 23, 2011).
Gray Leaf Spot of Perennial Ryegrass, Plant Management Network, http://www.plantmanagementnetwork.org/pub/php/diagnosticguide/2003/ryegrass/ (downloaded Aug. 23, 2011).
Herbicide List for Identification of Unknown Herbicides, Northeastern Collegiate Weed Science Contest, http://www.newss.org/docs/mop/addendum-9.pdf, (2007).
Herbicide Recommendations for Turfgrass: Postemergence Broadleaf Herbicides, Ontario Ministry of Agriculture, Food and Rural Affairs, http://www.omafra.gov.on.ca/english/crops/pub75/17turpbh.htm (downloaded Sep. 10, 2001).
Herbicide—Wikipedia, the free encyclopedia, http://en.wikipedia.org/wiki/Herbicide (downloaded Aug. 29, 2006).
"Horticultural Oils", http://www.ipmofalaska.com/files/hortoils.html, IPM of Alaska (downloaded Apr. 5, 2005).
Insect Pest Management on Golf Courses, Eileen A. Buss, University of Florida, http://edis.ifas.ufl.edu/in410 (downloaded Aug. 26, 2011).
Insect Pest Management on Turfgrass, Eileen A. Buss, University of Florida, http://edis.ifas.ufl.edu/ig001 (downloaded Aug. 26, 2011).
Integrated Pest Management—Identification & Management of Turfgrass Disease, University of Missouri, http://extension.missouri.edu/p/IPM1029 (downloaded Aug. 25, 2011).
"It pays to be pure", http://www.findarticles.com/p/articles/mi_qa3824/is_200405/ai_n9424665/print, Meister Media Worldwide, May 2004.
Online Guide to Plant Disease Control of Oregon State University Extension (http://plant-disease.ippc.orst.edu/) (downloaded May 16, 2005) and hardcopy version, "The 2004 PNW Plant Disease Management Handbook".
Performance of generic phosphite fungicides: A status report, AgNet Mar. 8, 2004, The Canadian Phytopathological Society, http://www.cps-scp.ca/pathologynews/performanceofgenericfungicides.html (downloaded Aug. 22, 2011).
Turf Tip, University of Arkansas, http://turf.uark.edu/turfhelp/archives/030509.html (downloaded Aug. 22, 2011).
Turfgrass Disease Profiles Dollar Spot, Purdue University, http://www.ces.purdue.edu/extmedia/BP/BP-105-W.pdf (downloaded Aug. 22, 2011).
Turfgrass Disease Profiles Gray Leaf Spot, Purdue University, http://www.ces.purdue.edu/extmedia/BP/BP-107-W.pdf (downloaded Aug. 23, 2011).
Turfgrass Insects Sheet 1, D.E. Short et al., University of Florida, http://edis.ifas.ufl.edu/in025 (downloaded Aug. 26, 2011).
Turfgrass Insects Sheet 2, D.E. Short et al., University of Florida, http://edis.ifas.ufl.edu/in026 (downloaded Aug. 26, 2011).
Turfgrass Pest Control, West Virginia University, http://www.wvu.edu/~exten/infores/pubs/pest/pcerti19.pdf (downloaded Aug. 22, 2011).
Understanding Bentgrass Dead Spot, USGA Turfgrass and Environmental Research Online, http://turf.lib.msu.edu/tero/v02/n02.pdf (downloaded Aug. 22, 2011).
Heil, Induced Systemic Resistance (ISR) Against Pathogens in the Context of Induced Plant Defences, Annals of Botany, 2002, 503-512, 89(5).
Lorbeer, Synergism, Antagonism, and Additive Action of Fungicides in Mixtures, Phytopathology, 1996, 1261-1262, 86(11).
Samoucha et al., Synergism in fungicide mixtures against Pseudoperonospora Cubensis, Phytoparasitica, 1988, 337-342, 16(4).
Vallad et al., Systemic Acquired Resistance and Induced Systemic Resistance in Conventional Agriculture, Crop Science, 2004, 1920-1934, 44.
Silicone Surface-Active Agents, Donna Perry, Dow Corning Corporation, http://www.dowcorning.com/content/publishedlit/26-1365.pdf (downloaded Aug. 30, 2011).
Turfgrass Diseases: Leaf Spots and Tip Blights, Melting Out, Crown and Root Rots, University of Rhode Island Landscae Horticulture Program, http://www.uri.edu/ce/factsheets/sheets/leafspotsetc.html (downloaded Aug. 30, 2011).
Leaf Spot and Melting-out (crown and root rot) Diseases—Center for Turfgrass Science, Penn State College of Agricultural Sciences, http://cropsoil.psu.edu/turf/extension/factsheets/managing-diseases/leaf-spot (downloaded Aug. 30, 2011).
Turfgrass Disease Profiles Leaf Spot/Melting Out, Purdue University, http://www.ces.purdue.edu/extmedia/bp/bp-103-w.pdf (downloaded Aug. 30, 2011).
Brown Patch, Center for Turfgrass Science, Penn State College of Agricultural Sciences, http://cropsoil.psu.edu/turf/extension/factsheets/managing-diseases/brown-patch (downloaded Aug. 30, 2011).
Brown Patch, University of Guelph, http://www.uoguelph.ca/pdc/Factsheets/PDFs/127TurfBrownPatch.pdf (downloaded Aug. 30, 2011).
Turfgrass Disease Profiles Brown Patch, Purdue University, http://www.ces.purdue.edu/extmedia/BP/BP-106-W.pdf (downloaded Aug. 30, 2011).
Brown Patch on Turfgrass, Cornell University Department of Plant Pathology and Plant-Microbe Biology, http://plantclinic.cornell.edu/factsheets/brownpatch.pdf (downloaded Aug. 30, 2011).
Turfgrass Disease Profiles Rhizoctonia Large Patch, Purdue University, http://www.extension.purdue.edu/extmedia/BP/BP-117-W.pdf (downloaded Aug. 30, 2011).
Nelson et al., 2,4-D and Mycoleptodiscus terrestris for Control of Eurasian Watermilfoil, J. Aquat. Plant Manage., 2005, 29-34, 43.
Office Action (Restriction Requirement) for U.S. Appl. No. 12/492,863 dated Aug. 15, 2011.
Material Safety Data Sheet for Killex Lawn Weed Control Concentate (Ortho), Scotts Canada Ltd., Sep. 13, 2005.
Label for Killex, Scotts, Canada Ltd., Jul. 23, 2001.
Specimen Label for Trimec Classic, PBI/Gordon Corporation, (2007).
Material Safety Data Sheet for Lambent MFF-199 SW, Lambent Technologies Corp., Jan. 31, 2005.
Material Safety Data Sheet for Lambent MFF 159-100, Lambent Technologies Corp., Apr. 4, 2006.
Material Safety Data Sheet for Silsurf A008-UP, Siltech Corporation, Aug. 21, 2009.
Material Safety Data Sheet for Sylgard 309 Silicone Surfactant, Dow Corning Corporation, Apr. 5, 2001.
Specimen Label for Trimec Southern, PBI/Gordon Corporation, (2007).
2,4-Dichlorophenoxyacetic acid—Wikipedia, the free encyclopedia, http://en.wikipedia.org/wiki/2%2C4-D (downloaded Aug. 29, 2006).
Scotts Canada Home: Killex Concentrate, http://scottscanada.ca/index.cfm/event/Product Guide.product/documentId/30B255B82B . . . (downloaded Aug. 2, 2006).

(56) References Cited

OTHER PUBLICATIONS

Notice for Mecoprop-P TGAC, Commonwealth of Australia Gazette No. NRA 3, Mar. 6, 2001.
Quicksheet for SALVO herbicide, UAP Canada, (2007).
Technical Data Sheet for Lambent MFF-199 SW, Lambent Technologies Corp., (2007).
Technical Data Sheet for Lambent MFF 159-100, Lambent Technologies Corp., (2007).
Technical Information for Lutensol AT types, BASF SE, (2007).
Product Information Sheet for Silgard 309 Silicone Surfactant, Dow Corning Corporation, (2007).
Technical Data Sheet for Silsurf A008-UP, Siltech Corporation, (2007).
Turfgrass Disease Profiles Gray Snow Mold, Purdue University, http://www.ces.purdue.edu/extmedia/BP/BP-101-W.pdf (downloaded Sep. 15, 2011).
Turfgrass Disease Profiles Pink Snow Mold and Microdochium Patch, Purdue University, http://www.ces.purdue.edu/extmedia/BP/BP-102-W.pdf (downloaded Sep. 15, 2011).
International Search Report for PCT International Application No. PCT/CA2007/001762, (2007).
Written Opinion for PCT International Application No. PCT/CA2007/001762, (2007).
International Preliminary Report on Patentability for PCT International Application No. PCT/CA2007/001762, (2007).
Office Action (Restriction Requirement) for U.S. Appl. No. 10/908,538 dated Feb. 26, 2009.
Office Action for U.S. Appl. No. 10/908,538 dated Apr. 1, 2009.
International Search Report for PCT International Application No. PCT/CA2009/000862, (2009).
Written Opinion for PCT International Application No. PCT/CA2009/000862, (2009).
Datapak for SALVO herbicide, United Agri Products Canada Inc., (2007).
International Preliminary Report on Patentability for PCT International Application No. PCT/CA2009/000862, (2009).
Examination Report for NZ Application No. NZ590318 dated May 6, 2011.
Office Action for CA Application No. CA2,507,482 dated Jan. 18, 2011.
Office Action for CA Application No. CA2,507,482 dated Aug. 11, 2009.
Cropper, Towards Reducing Fungicide Use in the Control of Dollar Spot (*Sclerotinia homoeocarpa* F.T. Bennett) Disease on Creeping Bentgrass (*Agrostis stolonifera* L.), Master of Science Thesis, University of Kentucky, http://archive.uky.edu/handle/10225/1044 (downloaded Sep. 15, 2011).
Kremer et al., Control of Sclerotinia homoeocarpa in Turfgrass Using Effective Microorganisms, EM World J., 2000, 16-21, 1(1).
Pest Control for Professional Turfgrass Managers 2011, North Carolina State University, http://www.turffiles.ncsu.edu/PDFFiles/004176/AG408PestControl_Professionals.pdf (downloaded Sep. 15, 2011).
Gilbert et al., Spring Greenup of Dormant Non-Overseeded Bermudagrass, University of Arizona College of Agriculture2004 Turfgrass and Ornamental Research Report, http://ag.arizona.edu/pubs/crops/az1359/az13593c11.pdf (downloaded Sep. 16, 2011).
Liu et al., Painting dormant bermudagrass putting greens, GCM, 86-91, Nov. 2007.
Shaposhnikov et al., Carboxy-substituted Phthalocyanine Metal Complexes, Russian Journal of General Chemistry, 2005, 1480-1488, 75(9).
Vol'Pin et al., Redox and fungicidal properties of phthalocyanine metal complexes as related to active oxygen, Journal of Inorganic Biochemistry, 2000, 285-292, 81(4).
Product Information Bulleting for SALVO, Platte Chemical Co., (2007).
Lincoln County Noxious Weed Control, http://www.co.lincoln.wa.us/WeedBoard/herbicide/herbicidefacts.pdf, (2007).
Characteristics of Plant Growth Regulators used in Fine Turf, Clemson University, http://www.clemson.edu/extension/horticulture/turf/pest_guidelines/2011_pest_guidelines/plant_growth_reg_2011.pdf (downloaded Aug. 24, 2011).
Chemical Update: Plant growth regulators, Grounds Maintenance, http://grounds-mag.com/mag/grounds_maintenance_chemical_update_plant_6/ (downloaded Aug. 24, 2011).
Ethephon and Trinexapac-ethyl Influence Creeping Bentgrass Growth, Quality, and Putting Green Performance, Plant Management Network, http://www.plantmanagementnetwork.org/pub/ats/research/2006/creeping/ (downloaded Aug. 24, 2011).
Evaluation of Commercially Available Plant Growth Regulator Programs for Creeping Bentrgrass Fairway Management, 2003, 2003 Annual Report—Purdue University Turfgrass Science Program, http://www.agry.purdue.edu/turf/report/2003/Page66.pdf#page=1 (downloaded Aug. 24, 2011).
Phytotoxicity, Food, Crop & Lifestock Safety, British Columbia Ministry of Agriculture, http://www.agf.gov.bc.ca/pesticides/e_10.htm (downloaded Aug. 26, 2011).
Phytotoxicity on Foliage Ornamentals Caused by Bactericides and Fungicides, A.R. Chase et al., Plant Pathology Fact Sheet, Florida Cooperative Extension Service, Institute of Food and Agricultural Sciences, University of Florida, http://plantpath.ifas.ufl.edu/takextpub/FactSheets/pp0030.pdf (downloaded Aug. 26, 2011).
Plant Growth Regulator Effects on Annual Bluegrass/Creeping Bentgrass Competition, Department of Crop & Soil Sciences Michigan State University, http://archive.lib.msu.edu/tic/mitgc/article/198852a.pdf (downloaded Aug. 24, 2011).
Plant Growth Regulator Regimens Reduce Poa annua Populations in Creeping Bentgrass, Plant Management Network, http://www.plantmanagementnetwork.org/pub/ats/research/2005/pgr/ (downloaded Aug. 24, 2011).
Plant Growth Regulators, University of Florida, http://edis.ifas.ufl.edu/pi139 (downloaded Aug. 24, 2011).
Plant Growth Regulators as a Turfgrass Management Tool, Greenkeeper, http://www.greenkeeper.com/upload/alinea_1425.pdf (downloaded Aug. 24, 2011).
Plant Growth Regulators for Fine Turf, Clemson University, http://www.clemson.edu/extension/horticulture/turf/pest_guidelines/growth_regulators.html (downloaded Aug. 24, 2011).
Plant Growth Regulators for Turf, Landscape and Garden, Lawn Care Academy, http://www.lawn-care-academy.com/plant-growth-regulators.html (downloaded Aug. 24, 2011).
Plant Growth Regulators: More Color, Less Clippings, Irrigation & green industry, http://www.igin.com/article-925-plant_growth_regulat.html (downloaded Aug. 24, 2011).
Plant Growth Regulators Used in Turfgrass Management, Georgia Turf, http://commodities.caes.uga.edu/turfgrass/georgiaturf/WeedMngt/weedcontrol/PGR.htm (downloaded Aug. 25, 2011).
Plant Growth Regulators Used in Turfgrass Management, Greenkeeper, http://www.greenkeeper.eu/upload/alinea_1420.pdf (downloaded Aug. 24, 2011).
Plant Growth Retardants for Fine Turf and Roadsides/Utilities, University of Florida, http://edis.ifas.ufl.edu/pdffiles/WG/WG06400.pdf (downloaded Aug. 24, 2011).
Putting the Numbers to PGRs, Grounds Maintenance, http://grounds-mag.com/chemicals/grounds_maintenance_putting_numbers_pgrs/ (downloaded Aug. 25, 2011).
Repeat Applications of Paclobutrazole (TGR) Plant Growth Regulator on Overseeded Bermudagrass Turf: Weed Control and Bermudagrass Transition, The 2009 Turfgrass, Landscape and Urban IPM Research Summary, The University of Arizona, http://ag.arizona.edu/pubs/crops/az1487/14875e.pdf (downloaded Aug. 24, 2011).
The Effect of the Plant Growth Regulator Primo on Winter Hardiness Levels, Prairie Turfgrass Research Centre, http://www.oldscollege.ca/ptrc/2004_ar/Primohardiness02-05.htm (downloaded Aug. 25, 2011).
Trinexapac-ethyl—PubChem Public Chemical Database, http://pubchem.ncbi.nlm.nih.gov/summary/summary.cgi?cid=92421&loc=ec_rcs (downloaded Aug. 25, 2011).
Turfgrass Growth Regulators for Professional Managers, Patrick E. McCullough, Extension Agronomist—Weed Science, Georgia Turf,

(56) References Cited

OTHER PUBLICATIONS http://commodities.caes.uga.edu/turfgrass/georgiaturf/Publicat/PCRP2011/PGR.pdf (downloaded Aug. 25, 2011).
Turfgrass Growth Regulators for Professional Managers, Tim R. Murphy, Extension Agronomist—Weed Science, Georgia Turf, http://commodities.caes.uga.edu/turfgrass/georgiaturf/Publicat/PCRP2009/PGR.09.pdf (downloaded Aug. 25, 2011).
Turfgrass quality and phytotoxicity affected by growth retardants, R.W. Duell, http://archive.lib.msu.edu/tic/its/articles/1985pro749.pdf (downloaded Aug. 24, 2011).
Use of Plant Growth Regulators to Retard Growth of Bermudagrass and Dallisgrass in the Landscape, Texas A&M University, http://www.tamu-commerce.edu/agscience/res-dlc/turf/pgr.html (downloaded Aug. 24, 2011).
Using plant growth regulators in turfgrass management. (Green Science)., Golfscape, http://www.highbeam.com/doc/1G1-105617663.html (downloaded Aug. 24, 2011).
Volume 3.3—Plant Growth Regulators Mode of Action, Australian Golf Course Superintendents' Association, http://www.agcsa.com.au/static/atm_articles/html/3_3c.html (downloaded Aug. 24, 2011).
Agnello, Petroleum-derived spray oils: chemistry, history, refining and formulation, in Beattie, G.A.C., Watson, D.M., Stevens, M., Spooner-Hart, R. and Rae, D.J. (eds). Spray Oils Beyond 2000—Sustainable Pest & Disease Management. University of Western Sydney, 2002.
Bakke, Analysis of Issues Surrounding the Use of Spray Adjuvants With Herbicides, 2002.
Blenis et al, Evaluation of Fungicides and Surfactants for Control of Fairy Rings Caused by Marasmius oreades (Bolt ex. Fr.) Fr., HortScience, 1997, 1077-1084, 32(6).
Burpee et al., Interactive Effects of Plant Growth Regulators and Fungicides on Epidemics of Dollar Spot in Creeping Bentgrass, Plant Disease, 1996, 1245-1250, 80(11).
Burpee and Latin, Reassessment of Fungicide Synergism for Control of Dollar Spot, Plant Disease, 2008, 601-606, 92(4).
Cline, OLR mating disruption just got easier, Western Farm Press, 2001, 1, 23(12).
Cockerham et al., Evaluation of Turfgrass Growth Retardant Chemicals, California Turfgrass Culture, 1971, 23-24, 21(3).
Colby, Calculating Synergistic and Antagonistic Responses of Herbicide Combinations, Weeds, 1967, 20-22, 20.
Coo-Ranger et al., Ionic Silicone Surfactants in Water-in-Silicone Oil Emulsions Containing Proteins, Polymer Preprints, 2004, 674-675, 45(1).
Cortes-Barco et al., Induced systemic rersistance against three foliar diseases of Agrostis stolonifera by an isoparaffin mixture, 2nd European Turfgrass Society Congress Proceedings, 2010, vol. 2.
Cortes-Barco et al., Induced systemic resistance against three foliar diseases of Agrostis stolonifera by (2R,3R)-butanediol or an isoparaffin mixture, Annals of Applied Biology, 2010, 179-189, 157(2).
Cortes-Barco et al., Comparison of induced resistance activated by benzothiadiazole, (2R,3R)-butanediol and an isoparaffin mixture against anthracnose of Nicotiana benthamiana, Plant Pathology, 2010, 643-653, 59(4).
Cranmer et al., Controlled droplet application (CDA) of fluazifop and sethoxydim for annual and perennial weed control, 1983 Meeting of the Weed Science Society of America, 1983, 23-24, Weed Abstract vol. 033 Abs. (No. 00871).
Crocker, Pesticide Screening Test for the Southern Chinch Bug, Journal of Economic Entomology, 1981, p. 730-731, 74(6).
Erhan et al., Comparisons of volatile organic chemical content of news, sheetfed, and heatset ink formulations, Journal of the American Oil Chemists' Society, 2001, 419-422, 78(4).
Findanza et al., Evaluation of fungicide and plant growth regulator tank-mix programmes on dollar spot severity of creeping bentgrass, Crop Protection, 2006, 1032-1038, 25(9).
Fidanza et al., Use of a Soil Surfactant with Fungicides for Control of Fairy Ring Disease in Turfgrass, Journal of ASTM International, 2007, 77-82, 4(4).
Furata, Strangers in a Strange Land, California Turfgrass Culture, 1971, 22-23, 21(3).
Gebhardt et al., Herbicide application with the controlled droplet applicator when using soybean oil, American Society of Agricultural Engineers Paper No. 83-1509, 1983, 12.
Guy et al., The performance of postemergence grass herbicides applied with sprinkler irrigation, Proceedings of the 39th annual meeting of the Southern Weed Science Society, 1986, 106, 8A (Abstract).
Hartzler, Role of spray adjuvants with postemergence herbicides, ISU Weed Science Online, Mar. 7, 2001, http:/www.weeds.iastate.edu/mgmt/2001/additives.htm (downloaded Aug. 19, 2011).
Hill, Silicone surfactants—new developments, Current Opinion in Colloid & Interface Science, 2002, 255-261, 7(5-6).
Hoffman, Analysis of Alcohol and Alkylphenol Polyethers via Packed Column Supercritical Fluid Chromatography, Ph.D. Thesis, VirginiaTech, Chapter 1, (2007).
Hsiang et al., Baseline sensitivity and cross-resistance to demethylation-inhibiting fungicides in Ontario isolates of Sclerotinia homoeocarpa, European Journal of Plant Pathology, 1997, 409-416, 103(5).
Hsiang et al., Sensitivity of Sclerotinia homoeocarpa to demethylation-inhibiting fungicides in Ontario, Canada, after a decade of use, Plant Pathology, 2007, 500-507, 56(3).
Jordan, Enhanced post-emergence herbicide efficacy with ultra-low volume application, Proceedings of the 48th annual meeting of the Southern Weed Science Society, 1995, 208-212, 48.
Nalewaja et al., Crop origin oils with grass control herbicides, Proceedings of the North Central Weed Control Conference, 1983, 3, 034 (Abstract).
Ostmeyer, The color Green, Golf Course Management, 1994, 40, 44, August.
Palla et al., Correlation of Dispersion Stability With Surfactant Concentration and Abrasive Particle Size for Chemical Mechanical Polishing (CMP) Slurries, Journal of Dispersion Science and Technology, 2000, 491-509, 21(5).
Pavlista, Paraffin enhances yield and quality of the potato cultivar Atlantic, Journal of Production Agriculture, 1995, 40-42, 8(1).
Perry, Ground Covers: Specifications and Costs, California Turfgrass Culture, 1971, 21-22, 21(3).
Puterka, Fungal pathogens for arthropod pest control in orchard systems: mycoinsecticidal approach for pear psylla control, BioControl, 1999, 183-210, 44(2).
Rieke, Thatchremoval, California Turfgrass Culture, 1971, 19-20, 21(3).
"The Stylet-Oil User's Guide", http://www.stylet-oil.com/ (downloaded Mar. 22, 2005).
Schott et al., Effects of adjuvants on herbicidal action. III. Effects of petroleum and rapeseed oils on diclofop-methyl action on ryegrass, Agronomie, 1991, 27-34, 11(1).
Shearman et al., Colorant Effects on Dormant Buffalograss Turf Performance, HortTechnology, 2005, 244-246, 15(2).
Trathnigg et al., Molecular Characterization of Ethoxylates by Complementary Chromatographic Techniques. Evaluation of Efficiency and Reliability, Tenside Surf. Det. 2003, 148-154, 40(3).
Tu et al., Weed Control Methods Handbook: Tools and Techniques for Use in Natural Areas, The Nature Conservancy Wildland Invasive Species Team, Apr. 2001.
Van Dam et al., A Turfgrass Colorant Study, California Turfgrass Culture, 1971, 17-19, 21(3).
Vincelli, Chemical Control of Turfgrass Diseases 2010, University of Kentucky College of Agriculture, http://pest.ca.uky.edu/PSEP/Manuals/ppa1.pdf (downloaded Aug. 22, 2011).
Walsh et al., Biology and Management of Dollar Spot (*Sclerotinia homoeocarpa*); an Important Disease of Turfgrass, HortScience, 1999, 13-21, 34(1).
Womack et al., A vegetable oil-based invert emulsion for mycoherbicide delivery, Biological Control, 1996, 23-28, 6(1).
Product Bulletin for Caltex, Caltex Australia, http://www.caltex.com.au/products_oil_detail_print.asp?id=229 (downloaded Aug. 2, 2006).

(56) References Cited

OTHER PUBLICATIONS

Yang et al., Infection of Leafy Spurge by Alternaria alternata and A. angustiovoidea in the Absence of Dew, Phytopathology, 1993, 953-958, 83(9).
Youngner, Kikuyugrass, *Pennisetum clandestinum*, and Its Control, Southern California Turfgrass Culture, 1958, 1-4, 8(1).
Youngner, Gibberellic Acid on Zoysia Grasses, Southern California Turfgrass Culture, 1958, 5-6, 8(1).
Youngner et al., Colorants for Dormant Bermuda and Other Subtropical Grasses, Southern California Turfgrass Culture, 1958, 7-8, 8(1).
Material Safety Data Sheet for Broadcoat Spray Adjuvant, Caltex Australia Limited, Sep. 2003.
Rhizoctonia Large Patch Disease of Zoysiagrass and Bermudagrass, University of Arkansas Division of Agriculture, http://www.uaex.edu/Other_Areas/publications/PDF/fsa-7527.pdf (downloaded Aug. 30, 2011).
Beasley et al., Trinexapac-ethyl and Paclobutrazol Affect Kentucky Bluegrass Single-Leaf Carbon Exchange Rates and Plant Growth, Crop Science, 2007, 132-138, 47.
McCowan, F.H., "Turf Herbicide Rx:Add Oil" Agricultural Chemicals. (1968), 23(4), pp. 18-21.
R.M. Goodwin et al., "Effect of Surfactants on Honey Bee Survival," New Zealand Plant Protection 53:230-234 (2000).
Edward L. Meister, Jr., "Pesticide Roundup," Farm Chemicals, 141(1), pp. 4, 38, 42, 44, 46, 48, 77, 78, 80, 82, 84, 86, 92, 94, 96 (1978).
International Search Report for PCT International Application No. PCT/CA2009/000862, 2009.
Material Safety Data Sheet for Chipco Signature, Bayer CropScience Pty Ltd, Oct. 21, 2002.
Material Safety Data Sheet for Chipco Signature, Bayer CropScience Pty Ltd, May 1, 2007.
Material Safety Data Sheet for Fore 80 WP Rainshield, Dow AgroSciences, Jun. 1, 2001.
Material Safety Data Sheet for Fore Fungicide, Rohm and Haas Company, Oct. 16, 1995.
Specimen Label for Fore 80WP Rainshield, Dow AgroSciences.
Specimen Label for Chipco Signature, Bayer CropScience Pty Ltd.
Pamphlet for Daconil, Syngenta Crop Protection Canada, Inc., http://www.mountainviewturf.com/our-products/pdf/ chemical-labels/Daconil.pdf.
Propiconazole Pesticide Information Profile, Extension Toxicology Network, http://pmep.cce.cornell.edu/profiles/extoxnet/metiram-propoxur/propiconazole-ext.html (downloaded Aug. 19, 2011).
Material Safety Data Sheet for Banner MAXX, Syngenta Crop Protection, Inc., Aug. 30, 2010.
Material Safety Data Sheet for Cleary 3336 Plus, Cleary Chemical Corporation, Feb. 1, 2005.
Material Safety Data Sheet for Rovral Green GT, Bayer CropScience Inc., Mar. 2, 2011.
Label for Banner MAXX, Syngenta Crop Protection, Inc.
Specimen Label for Cleary 3336 Plus, Cleary Chemical Corporation.
Label for Rovral Green GT, Bayer CropScienc Inc.
Pamphlet for Daconil Ultrex, Syngenta Crop Protection Canada, Inc., http://www.syngentacropprotection-us.com/pdf/labets/DACONIL-Ultrex-28354-en-pamphlet.pdf.
Office Action (Restriction Requirement) for U.S. Appl. No. 11/866,157 dated May 16, 2011.
Office Action for U.S. Appl. No. 11/866,157 dated Aug. 29, 2011.
Material Safety Data Sheet for Grass Greenzit, W.A.Cleary Chemical Corporation, Oct. 1997.
Material Safety Data Sheet for Green Lawnger, Becker Underwood, Inc., Feb. 25, 2009.
Material Safety Data Sheet for Regreen, Precision Laboratories, Inc., Mar. 1, 2010.
Label for Regreen, Precision Laboratories, Inc.
Technical Sheet for Green Lawnger, Becker Underwood, Inc.
Pigment Identification Charts, Golden Artist Colors.
Deformulation of RD 7212 Grazz Greenzit, 2009.
Effect of Chloro-Aluminum-Phtahalocyanine on the Growth of Lenma gibba G3-Ben-Tal, 1989.
Effects of Turf Colorants and FES04 on Spring Greenup of Zoysiagrass—Diesburg, 1990.
Grass Greenzit specimen label, 1998.
Kannar Product Range Turf Enhancing Products, 2007.
Material Safety Data Sheet—Kannar Green KC 200, 2007.
Material Safety Data Sheet—Kannar Tufkare Green, 2007.
Quantification of Phosphorous in Water Based Green Pigments, 2009.
The Development of Solid Spectral Filters for the Regulation of Plant Growth, 2008.
Turf Grass Coloration Using Hexadentate Cobalt Phthalocyanine amine, 1976.
Use of Cleary's Grass Greenzit—Cleary Chem Corp, 2004.
A Guide to NTEP Turfgrass Ratings—Morris, 2011.
Better Creeping Bentgrass Through Electricity—Huang, 2003.
Cytokinin Effects on Creeping Bentgrass Responses to Heat Stress—Liu, 2002.
Greass Greenzit Material Safety Data Sheet—Cleary, 2011.
Heat Stress Study Using Greenzit Pigment—U. of Guelph, 2009.
Overseed Greens Performance Trials—Kopeck, 2004.
"Emerald® Fungicide a Better Standard for Dollar Spot Control," Jan. 1, 2007 [retrieved on Jan. 14, 2014]. Retrieved from the Internet <URL: http://betterturf.basf.us/products/related-documents/emerald-info-sheet.pdf>, 2 pages.
"The National Turfgrass Research Initiative: Enhancing America's Beauty Protecting America's Natural Resources Ensuring the Health and Safety of all Americans," Retrieved from the Internet: <URL: http://www.ntep.org/pdf/turfinitiative.pdf>, Apr. 2003, 22 pages.
"Sunspray 6E—Material Safety Data Sheet," Jun. 1, 2009, [retrieved on Sep. 30. 2014]. Retrieved from the Internet: <URL: http://www.recarroll.com/cw3/Assets/product files/Sunspray 6E.pdf>, 5 pages.
Aerosil 200, Evonik [online] <URL: http://www.aerosil.com/lpa-productfinder/page/productsbytext/detail.html?pid=1855 &lang=en>, Jun. 19, 2012, 1 page.
Application of SK EnSpray Oil, Chen Zhengdon, Pesticide Science and Administration, 28(10)25-29, Dec. 31, 2007.
Beckerman, "Disease Management Strategies for Horticultural Crops: Using Organic Fungicides," Purdue Extension, Apr. 1, 2008 [retrieved on Sep. 29, 2014]. Retrieved from the Internet: <URL: https://www.extension.purdue.edu/extmedia/bp/bp-69-w.pdf>, 4 pages.
Bradley, "Some ways in which a paraffin oil impedes APHID transmission of potato virus Y," *Canadian Journal of Microbiology*, 9(3): 369-380, 1963.
Dell et al., "The Efficacy of JMS Stylet-Oil on Grape Powdery Mildew and Botrytis Bunch Rot and Effects on Fermentation," *Am. J. Enol. Vitic.*, 49(1):11-16, 1998.
Fertilome, "Broad Spectrum Landscape & Garden Fungicide (32 oz)," Fertilome.com [online] archived on Dec. 30, 2010. Retrieved from the Internet: <URL: http://web.archive.org/web/20101230174658/http://www.fertilome.com/product.aspx?pid=9950d7cl-dfed-4268-9474-eb508f967dc0>, 2 pages.
Gauvrit and Cabanne, "Oils for weed control: Uses and mode of action," *Pesticide Science*, 37(2):147-153, 1993.
Material Safety Data Sheet for Daconil 2787, Syngenta Crop Protection Canada, Inc., 7 pages, Dec. 31, 2008.
Material Safety Data Sheet for Daconil Ultrex Fungicide, Syngenta Crop Protection Canada, Inc., 7 pages, Aug. 1, 2009.
Mergos et al., "Dielectric properties of nanopowder emulsions in paraffin oil," 2011 IEEE International Conference on Dielectric Liquids, Sep. 8, 2011.
Mueller, "Fungicides: Qol Fungicides" Iowa State University, Available from: <URL: http://www.ipm.iastate.edu/ipm/icm/2006/5-22/fungicides.html>, 2 pages.
Mueller, "Fungicides: Triazoles," Intigrated Crop Management, Iowa State University, May 30, 2006. Retrieved from the Internet: <URL: http://www.ipm.iastate.edu/ipm/icm/2006/5-30/fungicides.htm >, 3 pages.
Oregon State University, National Forage & Grasslands Cirriculumn, "Discuss the basics of grass growth," forages.oregonstate.edu

(56) References Cited

OTHER PUBLICATIONS

[online] <URL: http://forages.oregonstate.edu/nfgc/eo/onlineforagecurriculum/instructormaterials/availabletopics/management/growth> copyright 2008, 6 pages.

Schutte et al., "Application of Azoxystrobin for Control of Benomyl-Resistant Guignardia citricarpa on 'Valencia' Oranges in South Africa," *Plant Dis.*, 87(7): 784-788, Jul. 2003.

Soomary et al., "Evaluation of Fungicides for Control of the Leaf Spot Disease Caused by Mycosphaerella eumusae on Banana in Mauritius," Food and Agricultural Research Council, Proceedings Fourth Annual Meeting of Agricultural Scientists, pp. 61-65, Feb. 2001.

The Seed Site, "Monocots and Dicots," captured Feb. 24, 2010. Retrieved from the Internet: <URL: http://web.archive.org/web/20100224074428/http://theseedsite.co.uk/monocot.html >, 2 pages.

Wicks, "Control of grapevine powdery mildew with mineral oil: an assessment of oil concentration and spray volume," *Australian Journal of Grape and Wine Research*, 5: 61-65, 1999.

European Search Report for Application No. 07866183.2, dated Jul. 24, 2013, pp. 1-7.

"Auxin," Wikipedia [online] Retrieved from the Internet: <URL: http://en.wikipedia.org/wiki/Auxin>, 12 pages, Retrieved on Apr. 9, 2015.

Engvild, "Herbicidal activity of 4-chloroindoleacetic acid and other auxins on pea, barley and mustard," Physiologia Plantarum, 96(2):333-337, Feb. 1996.

Holly Frontier®, "Sunspray Oils," 2014 [retrieved on Jul. 27, 2015]. Retrieved from the Internet: <URL: http://www.hollyfrontierlsp.com/Products/Horticultural-Oils/Sunspray-Oils/85/>, 1 page.

Product Information—Sunoco Sunspray 11N/11E, 1 page, 2009.

Heath et al., "Chelating agents and auxin," Nature, 201(4919):585-587, Feb. 8, 1964.

\* cited by examiner

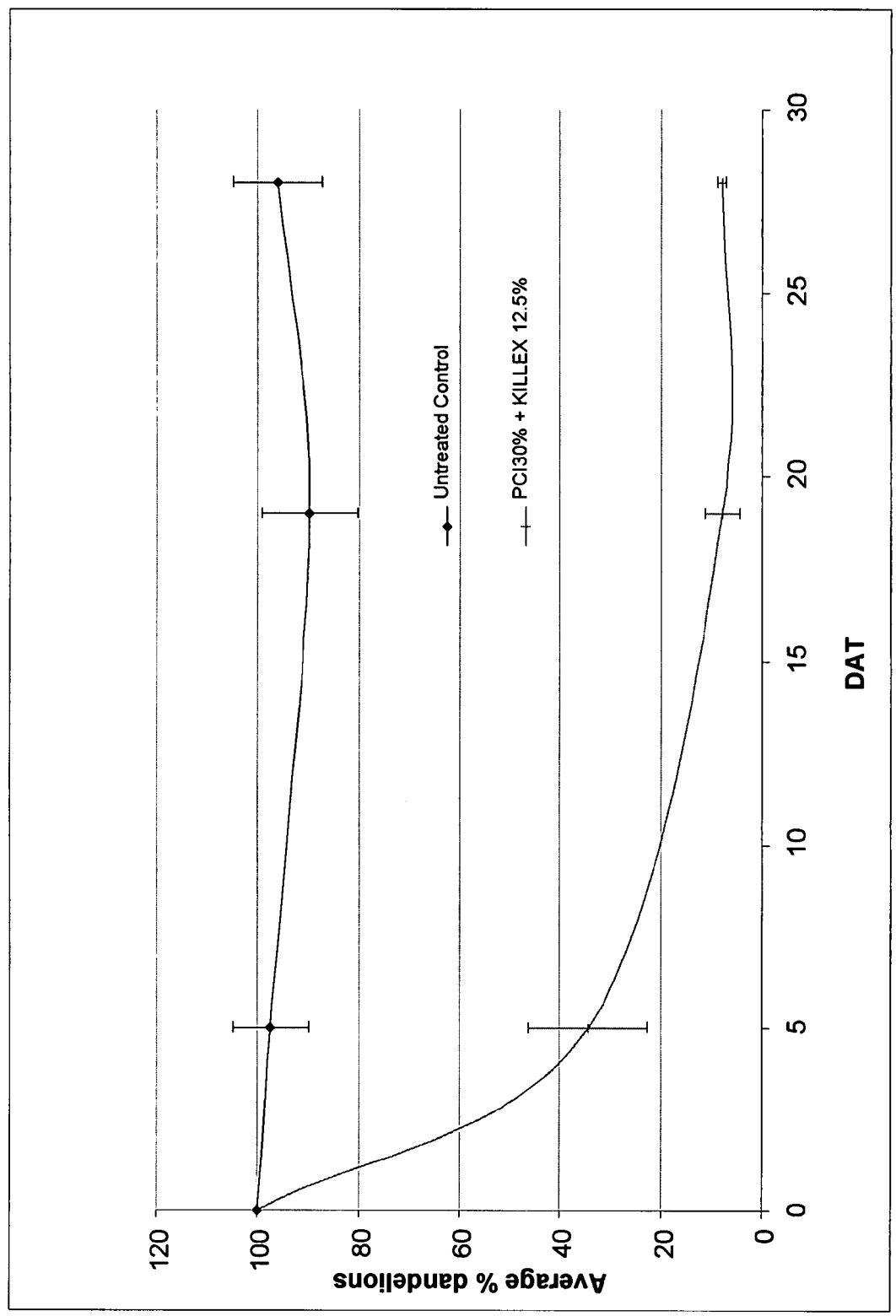

HERBICIDAL COMPOSITION WITH INCREASED HERBICIDAL EFFICACY

CROSS-REFERENCE TO RELATED APPLICATION

This application is a non-provisional application claiming priority of pending U.S. patent application Ser. No. 60/828,352, filed Oct. 5, 2006, the entirety of which is incorporated herein by reference.

FIELD OF THE INVENTION

The invention relates to herbicidal compositions and in particular to herbicidal oil-in-water emulsions that reduce the effective amount of herbicide required for the control of broadleaf weeds in turfgrass, while being substantially non-phytotoxic to turfgrass.

BACKGROUND OF THE INVENTION

The use of oils as herbicide adjuvants is a well established practice in agriculture for improvement of weed control applications through better coverage and penetration of the active ingredient on the leaf surface of the target weed. In many cases, this permits some degree of reduction in the rate of herbicide required, which is particularly desired for synthetic herbicides that are toxic to humans and the environment. Oil-based herbicide adjuvants are often formulated as an herbicidal "emulsifiable concentrate" consisting of a 75-95 wt % hydrocarbon oil or solvent with the balance being emulsifier, and to which the herbicide is added. In use, the herbicidal emulsifiable concentrate is diluted with water to form an oil-in-water emulsion which is then sprayed onto the target area at an appropriate rate.

While most oil-based herbicidal adjuvants have been directed to the control of grassy weeds in crops, little has been done with respect to the use of such adjuvants for the control of broadleaf (dicotyledous) weeds in turfgrass. In one study by McCowan (McCowan, F. H. "Turf Herbicide Rx: Add Oil" April, 1968), it was found that the addition of Sunspray Oil 11E (a mixture of refined paraffin oil and emulsifier at 98:2 wt %, respectively; available from Sunoco, Inc. Philadelphia Pa., USA) to certain herbicides resulted in equal or better weed control in turfgrass when delivered at a rate of 2 gallons of oil per acre. However, the herbicide oil combination also resulted in a significant increase in toxicity to the turfgrass in some cases. Overall, Applicant believes McCowan's findings were not conclusive with respect to the selectivity, effectiveness and phytotoxicity of various herbicide-oil combinations. To the inventor's knowledge, there are currently no high-oil-content herbicide compositions that selectively kill broadleaf weeds on the market for use on turfgrass.

Wide use of selective herbicides like 2,4-D (2,4 dichlorophenoxyacetic acid), Mecoprop (MCPP or methylchlorophenoxypropionic acid) and dicamba (3,6-dichloro-o-anisic acid) for controlling broadleaf weed in turfgrass throughout the world are controversial. The International Agency for Research on Cancer has classified the entire family of phenoxy-type herbicides, and particularly 2-4D, as potentially carcinogenic. Mecopropand dicamba are suspected of being human teratogens. In the interest of public safety, regulatory bodies such as US EPA and Health Canada PMRA have been making label improvements aimed primarily at exposure reduction of 2,4-D and other herbicides to environments.

Control of broadleaf weeds remains a major problem in turfgrass throughout the world. Further, public concerns related to human health and safety as well as the impact on environments resulting from the application of such herbicides, continue to arise. There is, therefore, a need in the art for improved herbicidal compositions for controlling broadleaf weeds in turfgrass that present a reduced risk to humans and to the environment.

SUMMARY OF THE INVENTION

Embodiments of the invention provide an herbicidal composition having an amount of active ingredient significantly reduced from known prescribed label rates used for conventional herbicides. The novel compositions demonstrate a significantly increased herbicidal efficacy for controlling broadleaf weeds in turfgrass while being substantially non-phytotoxic to the turfgrass.

Embodiments of the invention enable use of known herbicides at much lower active ingredient (A.I.) rates while showing at least equivalent broadleaf weed control in turfgrass when compared to prescribed label rates, typically expressed as the A.I. per unit area.

Embodiments of the invention are also directed to a method of controlling broadleaf weeds in turfgrass while being substantially non-phytotoxic to turfgrass, which comprises treating the locus thereof with an effective amount of the novel herbicidal composition. As an additional feature, embodiments of the novel herbicidal composition have been found to control insects, such as sod webworms and fall armyworms, in turfgrass.

Therefore in a broad aspect, embodiments of the herbicidal compositions having increased herbicidal efficacy comprise: a broadleaf herbicide in an effective amount of active ingredient per unit area reduced from about 90% to about 50% of a prescribed label rate, wherein the composition has low potential phytotoxicity for turfgrass when applied as an oil-in-water emulsion at a total spray volume of from about 60 to about 120 gal/acre, the oil-in-water emulsion further comprising an oil-emulsifier mixture having a ratio of oil to emulsifier from about 95:5 wt % to about 50:50 wt %.

Further, embodiments of the invention are emulsion-forming broadleaf herbicide concentrates comprising: a broadleaf herbicide in an effective amount of active ingredient per unit area reduced from about 90% to about 50% of a prescribed label rate, and an oil-emulsifier mixture having a ratio of oil to emulsifier from about 50:50 wt % to about 95:5 wt %, wherein when diluted in water as an oil-in-water emulsion for application to turfgrass at a total spray volume of from about 60 to about 120 gal/acre the concentrate has a low potential phytotoxicity for turfgrass.

Additionally, embodiments of the invention teach a method of preparing an oil-in-water emulsion having increased herbicidal efficacy and for delivery a reduced amount of active ingredient of an herbicide to turfgrass comprising: preparing an emulsion-forming broadleaf herbicide concentrate by combining a broadleaf herbicide in an effective amount of active ingredient per unit area reduced from about 90% to about 50% of a prescribed label rate, and an oil-emulsifier mixture having a ratio of oil to emulsifier from about 50:50 wt % to about 95:5 wt %; and combining the emulsion-forming broadleaf herbicide concentrate with water sufficient to dilute the oil-emulsifier from about 5 wt % to about 35 wt % for forming an oil-in-water emulsion for application to turfgrass at a total spray volume of from about 60 to about 120 gal/acre, the oil-in water emulsion having a low potential phytotoxicity for turfgrass.

Exemplary herbicides contemplated for use in embodiments of the invention are the auxin mimic-type herbicides which include such herbicides as KILLEX® and TRIMEC®.

BRIEF DESCRIPTION OF THE DRAWINGS

FIG. 1 is a graphical representation of the effect of KILLEX® formulations according to embodiments of the invention, as described in Example 3, over time.

DETAILED DESCRIPTION OF THE PREFERRED EMBODIMENT

As used herein, the term "control" generally refers to killing, inhibition of proliferation, or otherwise diminishing the occurrence of plants.

Further, the terms "turfgrass" or "grass" generally refer to grasses that are periodically cut or mowed to provide a groundcover for various utility, recreational or aesthetic purposes. Exemplary turfgrasses include Fescues, Rye, Bent, Bahia, St. Augustine, Centipede, Kentucky bluegrass, Zoysia Native Grasses (e.g., Buffalo grass, Blue Grama and Wheatgrasses), Seashore Paspalum, Carpet Grass, Buffo, and Beach Grass. Such grasses are typically found in locations such as parks, golf courses, sports fields, sod farms, roadsides, and lawns for housing residences, commercial sites, and institutional grounds.

Examples of "broadleaf weeds" include, but are not limited to, bedstraw, bindweed (field), birdsfoot trefoil, black medic, blackseed plantain, blueweed, broad-leaved plantain, burdock, buttercup, canada thistle, chickweed, chicory, clover, common chickweed, daisy fleabane, dandelion, devil's paint brush (hawkweed), dock (curled), english daisy, fall dandelion (fall hawkbit), grass leaved stitchwort, ground ivy, heal-all, henbit, knotweed, kochia, lamb's-quarters, mallow, mouse-ear chickweed, mustards, narrow-leaved plantain, ox-eye daisy, peppergrass, pigweed, pineapple weed, poison ivy, prostrate pigweed, purslane, ragweed, russian thistle, sandwort (thyme-leaved), sheep sorrel, shepherd's purse, smartweed (green), sow thistle, speedwell (purslane leaved), spotted spurge, stitchwort, stonecrop (mossy), veronica (thyme-leaved), wild lettuce, yellow hawkweed brambles, buckhorn plantain, bull thistle, carolina geranium, cocklebur, crudweed, evening primrose, false dandelion, fleabane, florida pusley, frenchweed poison oak, hawkweed, honeysuckle, jimsonweed, kudzu, little starwort, morning glory, oxalis (yellow woodsorrel), pennywort, plantains (narrow, buckhorn, broadleaf), poorjoe, povertyweed, soliva, spreadwell (annual), spurge, sumac, vervain, vetch, violet, wild aster, wild blackberry, wild carrot, wild garlic, wild geranium, wild onion, wild radish, wild raspberry and yarrow.

In embodiments of the invention, the herbicidal composition comprises a highly saturated oil, an emulsifier, and a broadleaf herbicide, provided as an oil-in-water emulsion (O/W emulsion) for ready-to-use applications or as an emulsifiable herbicidal concentrate which is thereafter diluted in water for application as the O/W emulsion.

In embodiments of the invention, the active ingredients (A.I.) of an herbicide selected to control broadleaf weeds are present in the oil-in-water emulsion in a range of from about a 50% reduction, compared to known prescribed label rates, to about a 90% reduction, compared to known prescribed label rates. The oil and emulsifier in the oil-emulsifier mixture are present in a weight ratio of about 95:5 wt % to about 50:50 wt %. The oil-emulsifier mixture is present in the total O/W emulsion at about 5% to about 35% by weight which is contemplated to be delivered in a total spray volume of about 60 to about 120 gallons of O/W emulsion per acre of turfgrass.

In embodiments of the invention the oil-emulsifier mixture is present in the total oil-in-water emulsion at about 10% to about 30%.

In embodiments of the invention the oil-emulsifier mixture comprises a ratio of oil to emulsifier of from about 85:15 wt % to about 90:10 wt %. The inventors have found that an oil-emulsifier mixture having less than about 5% of emulsifier does not significantly increase herbicidal efficacy, even when used at 30% in the O/W emulsion.

In embodiments of the invention, exemplary herbicides comprise auxin mimic or growth regulator type herbicides, which include the phenoxy-type herbicides, such as 2,4-D, 2,4-DB, 24-DP, benzoic acid-type herbicides, such as dicamba and MCPA and other aromatic acid herbicides such as clopyralid, fluoroxypyr, picloram and quinclorac.

It is particularly contemplated that the herbicide used is either KILLEX® (Scott Canada, Mississauga, Ontario) or TRIMEC® (PBI/GORDON Corporation, Kansas City, Mo.), both of which are combinations of 2,4-D Mecoprop and dicamba. In embodiments of the invention, KILLEX® or TRIMEC® are used in a total herbicide active ingredient to oil-emulsifier mixture ratio of about 1:50 to about 1:750 by weight.

In the case of KILLEX® or TRIMEC®, the 2,4-D may be in the form of an acid, a salt or an ester, such as 2,4-D acid, 2,4-D sodium salt, 2,4-D diethyl amine, 2,4-D dimethylamine salt, 2,4-D isopropyl acid, 2,4-D triisopropyl acid, 2,4-D butoxyethyl ester, 2,4-D ethylhexyl ester or 2,4-D isopropyl ester. The Mecoprop may be in the form of an acid, a salt or an ester, such as MCPP acid, potassium salt, dimethylamine salt, diethanolamine salt or isooctyl ester. The Dicamba may be in the form of an acid, a dimethylamine or a sodium salt.

Oils used in the composition are highly saturated oils. Typically, the oils are either synthetic or produced using conventional refining techniques such as solvent extraction, severe and mild hydrocracking or hydrotreating or hydrofining and have a viscosity in the range of about 6 cSt to about 34 cSt at 40° C. (ASTM 445). Embodiments of the invention utilize paraffinic or isoparaffinic oils.

In embodiments of the invention, isoparaffinic oils are selected to have a carbon number distribution in the range of about $C_{16}$ to about $C_{35}$ and is highly refined to have an aromatic content of less than about 10 wt % and in embodiments of the invention less than about 5 wt %. In embodiments of the invention an isoparaffinic oil having substantially no aromatics is selected.

As compared to "light oils" such as SOLVESSO™ 150 (available from ExxonMobil) or kerosene, the inventors believe heavier isoparaffinic oils evaporate less quickly from the leaf surface and do not cause severe cell membrane disruption and therefore provide a better opportunity for the O/W emulsion to spread and for the herbicide therein to penetrate the leaf surface effectively.

Emulsifiers are selected to have minimal toxicological risk, such as those included on the Environmental Protection Agency's List 3 or 4 Inert (other) Pesticide Ingredients in Pesticide Products. Appropriate emulsifiers are selected to have sufficient solvency in the oil phase such as described in U.S. Pat. No. 6,515,031 to Applicant, the entirety of which is incorporated herein by reference.

In embodiments of the invention, suitable emulsifiers also include ethoxylated alcohols having primary $C_5C_{20}$ carbon chains with an average of about 2 to about 7 ethoxylation groups and alkyl phenol ethoxylates, including but not limited to dodecyl phenol ethoxylates, nonyl phenol ethoxylates and the like.

Commercial preparations, whether prepared as ready-to-use compositions or as emulsifiable concentrates, may further contain such additional ingredients as are known to one of skill in the art, such as preservatives to extend the shelf-life stability. In embodiments of the invention, a small amount of preservative, such as methylchloroisothiazolinone in combination with methylisothiazolinone (KATHON® CG/ICP available from Rohm and Haas) is added, typically at less than 2.25 ppm of active ingredient.

The O/W emulsions to be sprayed on turfgrass are typically prepared using high shear mixing equipment such as a Polytron® Homogenizer (available from Kinematica Inc., Newark, N.J., USA). Preparation using high shear equipment results in stable emulsions which can then be applied to the turfgrass using conventional spraying equipment and techniques.

As shown in the examples below, the unique combinations of oil and emulsifier in the emulsions act to reduce the amount of active ingredient of the herbicide, particularly KILLEX® and TRIMEC®, required to kill broadleaf weeds in turfgrass as compared to conventional aqueous solutions of the same herbicides. The compositions as shown result in a lack of detectable phytotoxicity when the O/W emulsion is used at a total spray volume of about 60-120 gal/acre.

One of skill in the art would understand that embodiments of the invention using other herbicides such as listed above would similarly result in a significant reduction of the amount of active ingredient of the herbicide required to control broadleaf weeds in turf grass.

Further, Applicant has noted that embodiments of the invention are effective in controlling insects such as tropical sod webworm and fall armyworm when applied to turfgrass.

EXAMPLE 1

General Materials and Methods

Materials

The oils, emulsifiers and herbicides shown in Tables 1, 2 and 3 were used as indicated in the examples.

TABLE 1

Oils

| Oil | Component | Source |
|---|---|---|
| N65DW | Synthetic isoparaffinic oil | Petro-Canada* |

*Calgary, AB, Canada

TABLE 2

Emulsifiers

| Emulsifier | Components | Source |
|---|---|---|
| AL3313 | Polyoxyethyene lauryl ether, $C_{10}$ to $C_{16}$ alcohol ethoxylates, and glycerol oleate | Uniqema* |
| Atplus 300F | Non ionic surfactant blends | Uniqema* |

*New Castle, DE, USA

TABLE 3

Herbicides

| Herbicide | Component | Source |
|---|---|---|
| KILLEX® | 2,4-D, dimethylamine @ 190 g/l (2,4-dicholorophenoxyacetic acid, dimethylamine salt) Mecoprop-p, Dimethylamine @ 100 g/l, (2-(2-Methyl-4-chlorophenoxy)propionic acid, dimethylamine salt) Dicamba, Dimethylamine @ 18 g/l (Benzoic acid 3,6-dichloro-2-methoxy-, dimethylamine salt) | Scott Canada* |
| TRIMEC® Classic | 2,4-D, dimethylamine @ 25.93% (2,4-dicholorophenoxyacetic acid, dimethylamine salt) Mecoprop-p, Dimethylamine @ 13.85% (2-(2-Methyl-4-chlorophenoxy)propionic acid, dimethylamine salt) Dicamba, Dimethylamine @ 2.76% (Benzoic acid 3,6-dichloro-2-methoxy-, dimethylamine salt) | PBI/ Gordon** |
| TRIMEC® Southern | 2,4-D, dimethylamine @ 18.74% (2,4-dicholorophenoxyacetic acid, dimethylamine salt) Mecoprop-p, Dimethylamine @ 17.37% (2-(2-Methyl-4-chlorophenoxy)propionic acid, dimethylamine salt) Dicamba, Dimethylamine @ 3.85% (Benzoic acid 3,6-dichloro-2-methoxy-, dimethylamine salt) | PBI/ Gordon** |

*Mississauga, Ontario
**Kansas City, Missouri

Methods

Preparation and Use of Aqueous KILLEX® and TRIMEC® Formulations

Conventional aqueous KILLEX® solutions were prepared by diluting KILLEX® in water as appropriate for use at the label rate ("KILLEX 100%", 0.59 gal/acre) and at a reduced rate ("KILLEX 12.5%", 0.074 gal/acre, 87.5% reduction). In particular, "KILLEX 100%" was used at the label rate of 0.59 gal/acre in sufficient water (approximately 107 gal/acre). "KILLEX 12.5%" was used at a reduced rate of 0.074 gal/acre in sufficient water (approximately 107 gal/acre).

TRIMEC® Classic solutions were prepared by diluting TRIMEC® Classic in water as appropriate for use at the label rate ("TRIMEC 100%", 0.5 gal/acre) and at a reduced rate ("TRIMEC 12.5%", 0.0625 gal/acre), each used at a spray volume of about 62 gallons per acre.

TRIMEC® Southern solutions were prepared by diluting TRIMEC® Southern in water as appropriate for use at the label rate of 0.19 gal/acre ("TRIMEC® Southern 100%") and at a reduced rate of 0.0625 gal/acre ("TRIMEC® Southern 33%"), each used at a spray volume of about 62 gallons per acre.

Preparation and Use of KILLEX® or TRIMEC® Oil-in-Water Emulsion Formulations

KILLEX® or TRIMEC® O/W emulsions were generally prepared by tank-mixing the components using high shear equipment such as a Polytron® Homogenizer (available from Kinematica Inc., Newark, N.J., USA) so as to produce a stable emulsion for application to turfgrass.

Various compositions of oil, emulsifier, herbicide and water were prepared, according to embodiments of the invention, varying the oil and emulsifier at 10%, 20% or 30% by weight of the total solution as shown in the examples below. The O/W emulsions were used at a rate of from about 62 gal/acre to about 107 gal/acre.

Testing of KILLEX® and TRIMEC® Formulations

KILLEX® or TRIMEC® formulations according to the various examples were applied to 2 m×2 m plots of turfgrass. Turfgrass tested at the University of Guelph, Ontario, Canada predominantly comprised perennial ryegrass, with some Kentucky bluegrass and other perennial grasses. Turfgrass tested at Michigan State University, MI, USA comprised a mixture of Kentucky blue grass, rye grass and tall fescue grass. Turfgrass tested at University of Florida, FL, USA comprised bahia grass and St. Augustine grass. The formulations were applied using standard spray procedures, as is known in the art.

For measuring the effect of the KILLEX® and TRIMEC® formulations on the control of broadleaf weeds, the number of dandelions, clovers, dollarweeds or pusley present in each plot was counted before and after treatment with KILLEX® or TRIMEC® formulations.

For measuring phytotoxic effects of the KILLEX® or TRIMEC® formulations on the turfgrass, the turfgrass was analyzed by visual rating accompanied by instrumental assessment using a chlorophyll meter.

EXAMPLE 2

Effects of KILLEX® Dosage and an O/W Emulsion of KILLEX® on Dandelions

This example demonstrates the effect of aqueous KILLEX® formulations on dandelion counts when used at the label rate (0.59 gal/acre) and a reduced rate (12.5%, 0.074 gal/acre, 87.5% reduction), as well as the effect of an O/W emulsion formulation containing 30% by weight of oil plus emulsifier on the efficacy of KILLEX® at the reduced rate. The KILLEX® formulations were prepared and tested as described in Example 1, with the O/W emulsions being applied at a rate of 107 gal/acre. The results are shown below in Table 4.

TABLE 4

Dandelion (% cover) - 21 days after treatment

| Sample | KILLEX® Gal/acre | PCI Oil-emulsifier Oil | emulsifier | Dandelion % cover (21DAA*) |
|---|---|---|---|---|
| Control (untreated) | (none) | (none) | (none) | 14.0 |
| KILLEX 100% (label rate) | 0.59 | (none) | (none) | 5.0 |
| KILLEX 12.5% | 0.074 | (none) | (none) | 12.8 |
| KILLEX 12.5% + PCI 30% | 0.074 | 85 wt % N65DW | 15 wt % AI3313 | 3.5 |

*DAA—days after application

The results shown in Table 4 demonstrate that KILLEX®, formulated as an O/W emulsion according to an embodiment of the invention, has increased efficacy with reduced herbicide and therefore lower levels of KILLEX® can be used to control dandelions.

EXAMPLE 3

Effect of KILLEX® O/W Emulsion Over Time on Dandelions

This example demonstrates the effect of KILLEX® O/W emulsion over time on dandelion counts in turfgrass. KILLEX® was used at a rate of 0.074 gal/acre in an O/W emulsion containing N65DW:AL3313 at 85:15 wt % and diluted to 30% by weight in water ("PCI 30%+KILLEX® 12.5%"). The KILLEX® formulations were prepared and tested as described in Example 1. The control used was untreated turfgrass.

As shown in FIG. 1, KILLEX®, formulated as an O/W emulsion according to an embodiment of the invention, is effective in controlling dandelions over time, expressed as days after treatment (DAT).

EXAMPLE 4

Effects of TRIMEC® Dosage and an O/W Emulsion of TRIMEC® on White Clovers

Example 4 demonstrates the effect of aqueous TRIMEC® formulations on white clover counts when used at the label rate (0.5 gal/acre) and at a reduced rate (0.0625 gal/Acre, 87.5% reduction).

Further Example 4 demonstrates the effect on the efficacy of TRIMEC® at the reduced rate when used as an O/W emulsion formulation according to embodiments of the invention containing 10% by weight of oil plus emulsifier and 20% by weight of oil plus emulsifier The TRIMEC® formulations were prepared and tested as described in Example 1 at Michigan State University, with the O/W emulsions being applied at a rate of 62 gal/acre. The results are shown in Table 5 below.

TABLE 5

Clover (% cover) 24 days after treatment

| Sample | TRIMEC® (gal/acre) | PCI Oil-emulsifier Oil | emulsifier | Clover % cover (24DAA*) | Turf Injury** |
|---|---|---|---|---|---|
| Control (untreated) | (none) | (none) | (none) | 15.7 | 1.0 |
| TRIMEC 100% label rate | 0.5 | (none) | (none) | 1.3 | 1.0 |
| TRIMEC 12.5% | 0.0625 | (none) | (none) | 10 | 1.0 |
| TRIMEC 12.5% + PCI 10% | 0.0625 | 85 wt % N65DW | 15 wt % AI3313 | 1.3 | 1.0 |
| TRIMEC 12.5% + PCI 20% | 0.0625 | 85 wt % N65DW | 15 wt % AI3313 | 1.7 | 1.0 |

*days after application
**Rating range from 0 to 10, with 10 representing greatest injury (phytotoxicity)

The results in Table 5 demonstrate that TRIMEC® formulated as an O/W emulsion according to embodiments of the invention has increased efficacy and therefore significantly lower levels of TRIMEC® can be used to control clovers in turfgrass without increased phytotoxicity.

EXAMPLE 5

Effects of TRIMEC® Southern and an O/W Emulsion of TRIMEC® Southern on Dollarweed and Pusley Example 5 demonstrates the effect of an aqueous TRIMEC® Southern formulation on dollarweed and pusley counts when used at the label rate (0.19 gal/acre) and an O/W emulsion formulation containing 10% by weight of oil plus emulsifier according to a embodiment of the invention applied at a reduced rate (0.0625 gal/acre, 67% reduction).

The TRIMEC® Southern formulations were prepared and tested as described in Example 1 at University of Florida, with the O/W emulsions being applied at a rate of 62 gal/acre. The results are shown in Table 6 below.

TABLE 6

Pusley and Dollarweed (% cover) - 24 days after treatment

| Sample | TRIMEC® Southern (gal/acre) | PCI Oil-emulsifier Oil | PCI Oil-emulsifier emulsifier | Pusley % cover (28DAA*) | Dollar-weed % cover (28DAA*) |
|---|---|---|---|---|---|
| Control (untreated) | (none) | (none) | (none) | 100 | 72 |
| TRIMEC® Southern 100% label rate | 0.19 | (none) | (none) | 49 | 47 |
| TRIMEC® Southern 33% + PCI 10% | 0.0625 | 85 wt % N65DW | 15 wt % AI3313 | 39 | 42 |

*Days after application

The results in Table 6 demonstrate that TRIMEC® Southern formulated as an O/W emulsion according to an embodiment of the invention has increased efficacy and therefore significantly lower levels of TRIMEC® Southern can be used to control pusley and dollarweed.

EXAMPLE 6

Effect of KILLEX® and O/W Emulsions of KILLEX® on Turfgrass-Phytotoxicity

Example 6 demonstrates the phytotoxic effect of KILLEX® and various O/W emulsions of KILLEX® according to embodiments of the invention on turfgrass.

The KILLEX® formulations were prepared and tested as described in Example 1, with the O/W emulsions comprising oil plus emulsifier at 20% by weight in water. The formulations were applied at a total spray volume 107 gal/acre. The results are shown in Table 7 below.

TABLE 6

Turfgrass phytotoxicity - KILLEX® formulations applied at 0.0885 gal/acre

| Sample | Oil-emulsifier Oil | Oil-emulsifier Emulsifier | Phytotoxicity (scale 0-10)** |
|---|---|---|---|
| Control | (none) | (none) | 0.25 |
| KILLEX 12.5% | (none) | (none) | 0.25 |
| KILLEX 12.5% + PCI 20% | 85 wt % N65DW | 15 wt % AI3313 | 0.25 |
| KILLEX 12.5% + PCII 20% | 85 wt % N65DW | 15 wt % Atplus300 | 0.5 |
| KILLEX 12.5% + PCIII 20% | 50 wt % N65DW | 50 wt % Atplus300 | 0.25 |

**Phytotoxicity scale from 0 to 10, 10 representing greatest phytotoxicity

The results shown in Table 7 demonstrate that the ratio of oil to emulsifier and the type of emulsifier used in the oil-emulsifier mixture can affect the phytotoxic effects of KILLEX® in O/W formulations according to embodiments of the invention.

EXAMPLE 7

Effect of TRIMEC® O/W Emulsion on the Control of Tropical Sod Webworms

Applicant has found that TRIMEC® O/W emulsions, according to embodiments of the invention described herein, are also effective to control sod webworms and fall armyworms in turfgrass.

Example 7 demonstrates the effect of the O/W formulations according to embodiments of the invention on killing tropical sod webworm larvae on St. Augustinegrass.

The O/W formulation was prepared having a reduced rate of TRIMEC® (0.0625 gal/acre) containing 10% by weight of oil plus emulsifier. The field trial was carried out at University of Florida on St. Augustine grass. Ten medium sized tropical sod webworm larvae per PVC ring were used, the larvae in the rings being retained outside on turfgrass for 4 days after the application of the O/W emulsion. The O/W emulsion was applied at a rate of 80 gal/acre. Live larvae numbers were counted four days after application. The results are shown in Table 8 below.

TABLE 7

Live Tropical Sod Webworm larvae 4 days after treatment

| Treatment # | # live larvae - untreated Control (4DAA) | # live larvae - O/W herbicide emulsion treated plot (4DAA) |
|---|---|---|
| 1 | 4 | 2 |
| 2 | 4 | 0 |
| 3 | 7 | 2 |
| 4 | 7 | 1 |
| 5 | 4 | 5 |
| 6 | 5 | 1 |
| 7 | 7 | 5 |
| 8 | 5 | 1 |
| 9 | 6 | 3 |
| mean | 5.44 | 2.22 |
| % control | 0 | 59.18 |

The results in Table 8 demonstrate that TRIMEC® formulated as an O/W emulsion according to an embodiment of the invention is effective to control sod webworms in turfgrass.

The embodiments of the invention in which an exclusive property or privilege is claimed are defined as follows:

1. An emulsion-forming herbicidal composition consisting essentially of:
   two or more broadleaf herbicides in an effective amount;
   a synthetic isoparaffinic oil and an emulsifier, wherein the wt % ratio of oil to emulsifier is from about 95:5 to about 50:50;
   one or more preservatives; and
   water;
   wherein:
   the effective amount of the two or more broadleaf herbicides is from about 10% to about 50% of a prescribed label rate for the broadleaf herbicides; and
   the emulsion-forming herbicidal composition has from about 5 wt % to about 10 wt % of the oil and emulsifier.

2. The composition of claim 1 wherein the wt % ratio of oil to emulsifier is from about 85:15 to about 90:10.

3. The composition of claim 1 wherein at least one of the two or more broadleaf herbicides comprises an auxin mimic-type herbicide.

4. The composition of claim 3 wherein two or more broadleaf herbicides are selected from a group consisting of:

2,4-dichlorophenoxyacetic acid in the form of an acid, a salt, an ester, or combinations thereof;
2-(2methyl-4-chlorophenoxy)propionic acid, in the form of an acid, a salt, an ester or combinations thereof; and
3,6-dichloro-o-anisic acid in the form of an acid, a salt, or combinations thereof.

5. The composition of claim 1 wherein the emulsifier comprises an ethoxylated alcohol.

6. The composition of claim 1 wherein the wt % ratio of oil to emulsifier is from greater than about 80:20 to about 95:5.

7. The composition of claim 1 wherein the wt % ratio of oil to emulsifier is about 85:15.

8. The composition of claim 1 wherein one of the two or more broadleaf herbicides comprises at least one herbicide selected from the group consisting of:
2,4-dichlorophenoxyacetic acid in the form of an acid, a salt, an ester, or combinations thereof;
4-(2,4-dichlorophenoxy)butyric acid in the form of an acid, a salt, an ester, or combinations thereof;
2-(2,4-dichlorophenoxy)propionic acid in the form of an acid, a salt, an ester, or combinations thereof;
dicamba in the form of an acid, a salt, or combinations thereof;
2-methyl-4-chlorophenoxyacetic acid in the form of an acid, a salt, an ester, or combinations thereof;
2-(2-methyl-4-chlorophenoxy)propionic acid in the form of an acid, a salt, an ester, or combinations thereof;
clopyralid in the form of an acid, a salt, an ester, or combinations thereof;
fluoroxypyr in the form of an acid, a salt, an ester, or combinations thereof;
picloram in the form of an acid, a salt, an ester, or combinations thereof; and
quinclorac.

9. The composition of claim 1 wherein at least one of the two or more broadleaf herbicides comprises at least one of the herbicides selected from the group consisting of:
2,4-dichlorophenoxyacetic acid in the form of an acid, a salt, an ester, or combinations thereof;
2-(2-methyl-4-chlorophenoxy)propionic acid, in the form of an acid, a salt, an ester or combinations thereof; and
3,6-dichloro-o-anisic acid in the form of an acid, a salt, or combinations thereof.

10. The composition of claim 1 wherein the emulsifier comprises polyoxyethylene lauryl ether, C10 to C16 alcohol ethoxylates, and glycerol oleate.

11. The composition of claim 4 wherein the wt % ratio of oil to emulsifier is from about 85:15 to about 90:10.

12. The composition of claim 4 wherein the wt % ratio of oil to emulsifier is about 85:15.

13. The composition of claim 4 wherein the emulsifier comprises an ethoxylated alcohol.

14. The composition of claim 4 wherein the emulsifier comprises polyoxyethylene lauryl ether, C10 to C16 alcohol ethoxylates, and glycerol oleate.

15. The composition of claim 1, wherein the one or more preservatives comprises methylchloroisothiazolinone in combination with methylisothiazolinone.

16. An emulsion-forming herbicidal composition consisting essentially of:
two or more broadleaf herbicides in an effective amount;
a paraffinic oil and an emulsifier, wherein the wt % ratio of oil to emulsifier is from about 95:5 to about 50:50;
one or more preservatives; and
water;
wherein:
the effective amount of the two or more broadleaf herbicides is from about 10% to about 50% of a prescribed label rate for the two or more broadleaf herbicides; and
the emulsion-forming herbicidal composition has from about 5 wt % to about 10 wt % of the oil and emulsifier.

17. The composition of claim 16 wherein at least one of the two or more broadleaf herbicides comprises an auxin mimic-type herbicide.

18. The composition of claim 17, wherein the two or more broadleaf herbicides are selected from the group consisting of:
2,4-dichlorophenoxyacetic acid in the form of an acid, a salt, an ester, or combinations thereof;
2-(2methyl-4-chlorophenoxy)propionic acid, in the form of an acid, a salt, an ester or combinations thereof; and
3,6-dichloro-o-anisic acid in the form of an acid, a salt, or combinations thereof.

19. The composition of claim 16, wherein the emulsifier comprises an ethoxylated alcohol.

20. The composition of claim 16, wherein the wt % ratio of oil to emulsifier is from greater than about 80:20 to about 95:5.

21. The composition of claim 16, wherein the wt % ratio of oil to emulsifier is about 85:15.

22. The composition of claim 16 wherein one of the two or more broadleaf herbicides comprises at least one herbicide selected from the group consisting of:
2,4dichlorophenoxyacetic acid in the form of an acid, a salt, an ester, or combinations thereof;
4-(2,4-dichlorophenoxy)butyric acid in the form of an acid, a salt, an ester, or combinations thereof;
2-(2,4-dichlorophenoxy)propionic acid in the form of an acid, a salt, an ester, or combinations thereof;
dicamba in the form of an acid, a salt, or combinations thereof;
2-methyl-4-chlorophenoxyacetic acid in the form of an acid, a salt, an ester, or combinations thereof;
2-(2-methyl-4-chlorophenoxy)propionic acid in the form of an acid, a salt, an ester, or combinations thereof;
clopyralid in the form of an acid, a salt, an ester, or combinations thereof;
fluoroxypyr in the form of an acid, a salt, an ester, or combinations thereof;
picloram in the form of an acid, a salt, an ester, or combinations thereof; and
quinclorac.

23. The composition of claim 16, wherein at least one of the two or more broadleaf herbicides comprises at least one of the herbicides selected from the group consisting of:
2,4-dichlorophenoxyacetic acid in the form of an acid, a salt, an ester, or combinations thereof;
2-(2-methyl-4-chlorophenoxy)propionic acid, in the form of an acid, a salt, an ester, or combinations thereof; and
3,6-dichloro-o-anisic acid in the form of an acid, a salt, or combinations thereof.

24. The composition of claim 16, wherein the emulsifier comprises polyoxyethylene lauryl ether, C10 to C16 alcohol ethoxylates, and glycerol oleate.

25. The composition of claim 18, wherein the wt % ratio of oil to emulsifier is from about 85:15 to about 90:10.

26. The composition of claim 18, wherein the wt % ratio of oil to emulsifier is about 85:15.

27. the composition of claim 18, wherein the emulsifier comprises an ethoxylated alcohol.

28. The composition of claim 18, wherein the emulsifier comprises polyoxyethylene lauryl ether, C10 to C16 alcohol ethoxylates, glycerol oleate.

29. The composition of claim 16, wherein the one or more preservatives comprises methylchloroisothiazolinone in combination with methylisothiazolinone.

30. An emulsion-forming herbicidal composition comprising:
two or more broadleaf herbicides in an effective amount;
a paraffinic oil and an emulsifier, wherein the wt % ratio of oil to emulsifier is from about 95:5 to about 50:50;
one or more preservatives; and
water;
wherein:
the effective amount of the two or more broadleaf herbicides is from about 10% to about 50% of a prescribed label rate for the two or more broadleaf herbicides;
the emulsion-forming herbicidal composition has from about 5 wt % to about 10 wt % of the oil and emulsifier; and
the composition does not include a lower alkanol ester of a long chain carboxylic acid, an an anionic surfactant derived from esterification of a polyoxyalkylene nonionic surfactant with a dihydric or trihydric inorganic acid or by carboxylation with an organic acid derivative, or a long chain carboxylic acid.

31. The composition of claim 30 wherein at least one of the two or more broadleaf herbicides comprises an auxin mimic-type herbicide.

32. The composition of claim 31, wherein the two or more broadleaf herbicides are selected from the group consisting of:
2,4-dichlorophenoxyacetic acid in the form of an acid, a salt, an ester, or combinations thereof;
2-(2-methyl-4-chlorophenoxy)propionic acid, in the form of an acid, a salt, an ester or combinations thereof; and
3,6-dichloro-o-anisic acid in the form of an acid, a salt, or combinations thereof.

33. The composition of claim 30, wherein the emulsifier comprises an ethoxylated alcohol.

34. The composition of claim 30, wherein the wt % ratio of oil to emulsifier is from greater than about 80:20 to about 95:5.

35. The composition of claim 30 wherein one of the two or more broadleaf herbicides comprises at least one herbicide selected from the group consisting of:
2,4dichlorophenoxyacetic acid in the form of an acid, a salt, an ester, or combinations thereof;
4-(2,4-dichlorophenoxy)butyric acid in the form of an acid, a salt, an ester, or combinations thereof;
2-(2,4-dichlorophenoxy)propionic acid in the form of an acid, a salt, an ester, or combinations thereof;
dicamba in the form of an acid, a salt, or combinations thereof;
2-methyl-4-chlorophenoxyacetic acid in the form of an acid, a salt, an ester, or combinations thereof;
2-(2-methyl-4-chlorophenoxy)propionic acid in the form of an acid, a salt, an ester, or combinations thereof;
clopyralid in the form of an acid, a salt, an ester, or combinations thereof;
fluoroxypyr in the form of an acid, a salt, an ester, or combinations thereof;
picloram in the form of an acid, a salt, an ester, or combinations thereof; and
quinclorac.

36. The composition of claim 30, wherein the emulsifier comprises polyoxyethylene lauryl ether, C10 to C16 alcohol ethoxylates, glycerol oleate.

37. The composition of claim 30, wherein the one or more preservatives comprises methylchloroisothiazolinone in combination with methylisothiazolinone.

* * * * *